United States Patent [19]

Hutson, Jr.

[11] 4,041,099
[45] Aug. 9, 1977

[54] PARAFFIN DEHYDROGENATION USING PLATINUM-TIN PROMOTED ZINC ALUMINATE CATALYST AND SILICA-FREE PARTICLES

[75] Inventor: Thomas Hutson, Jr., Bartlesville, Okla.

[73] Assignee: Phillips Petroleum Company, Bartlesville, Okla.

[21] Appl. No.: 720,317

[22] Filed: Sept. 3, 1976

Related U.S. Application Data

[62] Division of Ser. No. 216,100, Jan. 7, 1972, Pat. No. 4,005,985.

[51] Int. Cl.$^2$ ............................................. C07C 5/36
[52] U.S. Cl. ............................... 260/683.3; 23/288 R; 208/143; 260/666 A; 260/668 D

[58] Field of Search ............... 260/683.3, 683, 666 A, 260/668 D; 23/288 R

[56] References Cited

U.S. PATENT DOCUMENTS

| | | | |
|---|---|---|---|
| 2,988,579 | 6/1961 | Watkins | 260/683.3 |
| 3,240,698 | 3/1966 | Leak | 208/143 |
| 3,247,276 | 4/1966 | Child et al. | 260/683.3 |
| 3,932,548 | 1/1976 | Rausch | 260/683.3 |

Primary Examiner—Veronica O'Keefe

[57] ABSTRACT

A method and an improved platinum-tin promoted zinc aluminate catalyst reactor for dehydrogenation of a paraffinic hydrocarbon feed stream as first and second layers of silica-free particles, each positioned in contact with and on opposed surfaces of the catalyst across the direction of feed stream flow through the reactor for preventing the poisoning of said catalyst.

3 Claims, 1 Drawing Figure

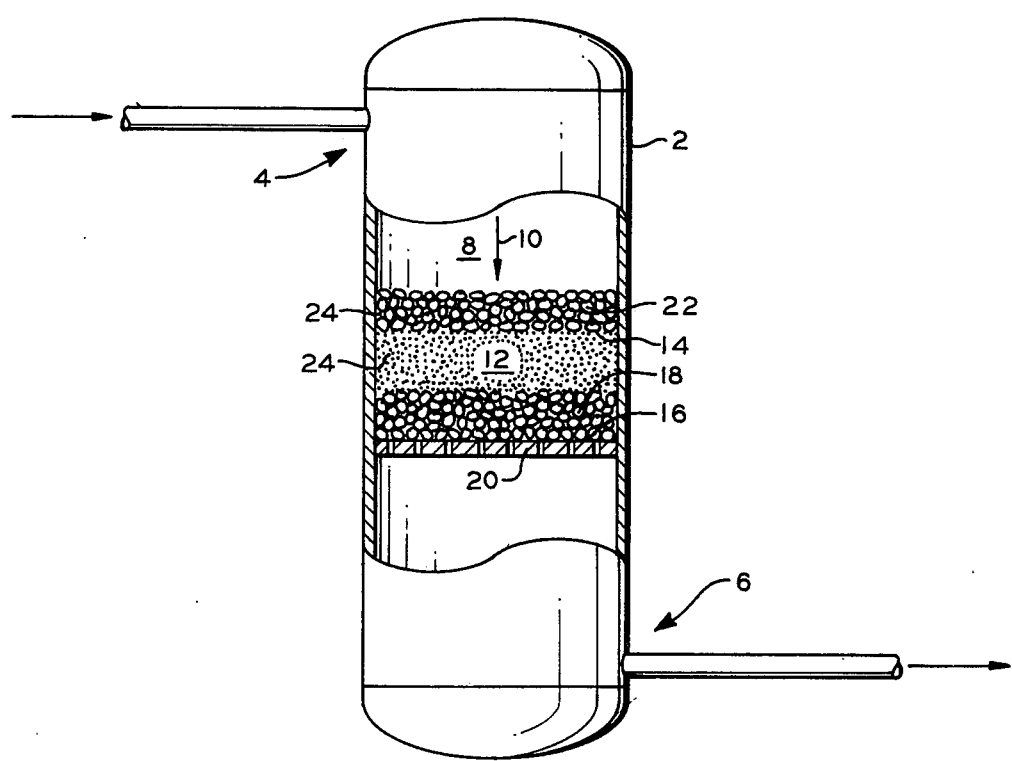

PARAFFIN DEHYDROGENATION USING PLATINUM-TIN PROMOTED ZINC ALUMINATE CATALYST AND SILICA-FREE PARTICLES

This is a divisional application of my copending patent application Ser. No. 216,100, filed Jan. 7, 1972, now allowed now U.S. Pat. No. 4,005,985.

In the operation of platinum-tin promoted zinc aluminate catalyst reactors, a great deal of difficulty has been encountered by said catalyst becoming prematurely deactivated. After a great deal of investigation, it was discovered that the materials that were considered inert materials suitable for use as hold down beds for catalyst reactors were, in fact, poisoning agents where the catalyst utilized was a platinum-tin promoted zinc aluminate catalyst and the feed stream was paraffinic hydrocarbon such as for example propane, butane, and alkanes such as cycloalkanes and arylalkanes, and was passed through the reactor for dehydrogenation thereof.

Examples of the materials used for hold down materials which caused premature deactivation were materials containing $SiO_2$ such as quartz chips, glass chips, bauxite and alundum for example.

This invention, therefore, resides in an apparatus and method for preventing the poisoning of a platinum-tin promoted zinc aluminate catalytic reactor being utilized for paraffinic hydrocarbon dehydrogenation by providing first and second layers of a silica-free material on opposed sides of and in contact with the catalyst traverse the direction of feed stream flow through the catalyst. In a preferred embodiment of this invention, stainless steel particles are used as the material for forming the first and second layers.

Other aspects, objects and advantages of the present invention will become apparent from a study of the disclosure, the appended claims and the drawing.

The drawing is a diagrammatic view of a platinum-tin promoted zinc aluminate catalyst reactor of this invention. The reactor 2 is of any suitable design generally insulated and provided with an inlet end portion 4, an outlet end portion 6, and a chamber 8 extending through the reactor in communication with the inlet 4 and outlet 6 for the passage of a material feed stream through the chamber 8 of the reactor from the inlet to the outlet in a flow direction shown by arrow 10.

The catalytic reactor 2 has a catalyst bed 12 therein which extends across the chamber 8 traversing the direction of flow of the feed stream therethrough. The catalyst is for example a platinum-tin promoted zinc aluminate catalyst that is utilized for dehydrogenation of a paraffinic hydrocarbon material feed stream that is passed through the reactor in contact with the catalyst 12. It should be understood that the platinum-tin promoted zinc aluminate catalyst is not considered herein as the invention, but it has been discovered that the operational life of this unique catalyst, when used for dehydrogenation of paraffinic hydrocarbons can be significantly extended by the use of the method and apparatus of this invention as opposed to the methods and apparatus heretofore utilized.

The example catalyst was prepared by dissolving 7.87 kg of hydrated zinc nitrate and 20.455 kg of hydrated aluminum nitrate in 10 gallons of deionized water. This solution and concentrated ammonia water (28 weight per cent $NH_3$) were separately added to 50 gallons of deionized water with stirring over a one-hour period, the addition rates being adjusted such that the pH was constant at about 7.5. The mixture was stirred two additional hours, and allowed to stand for three days. The precipitate was washed two times by reslurrying in 50 gallons of fresh water, spray-dried at about 925° F, dried in an oven about 17 hours at 625° F, formed into ¼-inch pellets and ground three times, calcined in air at about 1000° F for about 36 hours, and steamed about 5 hours at about 1025° F and used in the form of 10–20 mesh granules. The zinc aluminate granules were calcined 3 hours at 1050–1100° F and then impregnated with sufficient chloroplatinic acid and stannous chloride to result in a catalyst which contained, based on the weight of the support, 0.4 weight per cent platinum and 1.0 weight per cent tin.

The platinum-tin promoted zinc aluminate catalyst layer 12 has an upper surface 14 and a lower surface 18 when positioned in the reactor 2 as set forth above. A first layer 18 of silica-free particles are positioned in contact with the lower surface 16 of the catalyst in the chamber 8 between the catalyst 12 and the outlet 6 of the reactor 2. The first layer 18 covers substantially the entire lower surface 14 of the catalyst and is supported by a supporting tray 20 having openings formed therethrough for the flow of the feed stream therethrough. The supporting tray 20 is of any construction known in the art for maintaining catalyst beds within the reactor 2.

The second layer 22 of silica-free particles is positioned in contact with the upper surface 14 of the catalyst 12 in the chamber 8 between the catalyst and the inlet 4 of the reactor 2. The second layer 22 covers substantially the entire upper surface of the catalyst. Both of the first and second layers 16, 22 extend traversely across the chamber 8 relative to the direction of flow of the material feed stream through the reactor 2.

It is preferred in the invention that the particles which form the first and second layers 16, 22 be stainless steel particles. A list of the types of stainless steel that can be utilized in this invention can be found in the *Encyclopedia of Chemical Technology*, Kirk-Othmer 2nd Edition, Vol. 18, pages 784–794 (1969). Examples of those types are: Type No. 302, 321, 347, 304L, and 316. Stainless steels that can be used are iron-chromium and iron-chromium-nickel. Stainless steel should not contain silicon, such as D319 which contains 1% silicon. Other particles that can be used as hold-down material are: metals and alloys, such as copper, brass, bronze, nickel and iron, which contain no silicon or silica.

In order to provide first and second layers 18, 22 that do not significantly and/or detrimentally restrict the feed stream flow through the reactor, it is preferred that the total of the void spaces 24 of each first and second layer per unit volume of said respective layer 18, 22 be substantially equal or greater than about the total void space 24 per unit length of the catalyst 12.

In the method of this invention, the first and second layers 18, 22 of the silica-free, preferably stainless steel, particles are maintained in contact with the platinum-tin promoted zinc aluminate catalyst 12 in the relative positions with the reactor 2 as set forth above. The surfaces of the catalyst across the catalytic layer is thereby prevented from contacting any silica containing particles which function to deactivate or poison said catalyst 12 such as bauxite, alundum, quartz for example as set forth above. The principal poisoning material that heretofore was believed to be inert is silica-containing particles such as quartz. However, in contact with this catalyst, it is surprisingly discovered that heretofore utilized materials that were heretofore considered inert, in this case, were in fact not inert.

The following examples show the poisoning effect of silica in the above named catalyst and how this poisoning or deactivating effect was avoided by specifically utilizing first and second layers of stainless steel particles.

EXAMPLE

Alternate layers of catalyst hold-down solids and catalyst were used in all runs in this cyclic, fixed bed, downflow operation. The top layer in each run was hold-down material at a depth of 12 to 14 inches. Below this top layer were four sections consisting of a one-inch layer of catalyst and a 5-inch layer of hold-down material. Below the last 5inch layer of hold-down material was a one-inch layer of catalyst and a final lowest layer of hold-down material having a depth of 12 to 17 inches. The catalyst in both runs was platinum and tin promoted zinc aluminate dehydrogenation catalyst.

The example catalyst was prepared by dissolving 7.87 kg of hydrated zinc nitrate and 20.455 kg of hydrated aluminum nitrate in 10 gallons of deionized water. This solution and concentrated ammonia water (28 weight per cent NH$_3$) were separately added to 50 gallons of deionized water with stirring over a one-hour period, the addition rates being adjusted such that the pH was constant at about 7.5. The mixture was stirred two additional hours, and allowed to stand for three days. The precipitate was washed two times by reslurrying in 50 gallons of fresh water, spray-dried at about 925°F, dried in an oven about 17 hours at 625°F, formed into ¼-inch pellets and ground three times, calcined in air at about 1000°F for about 36 hours, and steamed about 5 hours at about 1025°F and used in the form of 10–20 mesh granules. The zinc aluminate granules were calcined 3 hours at 1050–1100°F and then impregnated with sufficient chloroplatinic acid and stannous chloride to result in a catalyst which contained, based on the weight of the support, 0.4 weight per cent platinum and 1.0 weight per cent tin.

Spectrographic analysis of used and unused catalysts of the above-described types disclose an increase of 0.4 weight percent in the silica content of the used catalyst. A zinc aluminate catalyst impregnated with 0.4 weight percent platinum and 1.0 weight percent tin was installed in a heated reactor as set forth above. The reactor was a 1.25 inch ID by 45 inch length tube positioned vertically in an electric furnace. Outlet temperature was 1100°F, pressure 85 psig.

Where quartz chips were utilized in the same manner and under the same operating conditions as silica-free stainless steel for forming the first and second layers, a spectrographic analysis of the catalyst where quartz chips were utilized showed silica concentrations of 0.3 to 3.0 weight percent on the catalyst but where the first and second layers were formed of silica-free stainless steel tubing having about ⅛-inch diameter and a length of about 3/16-inch, there was no evidence of catalyst deactivation or poisoning as determined by spectrographic analysis.

This example, therefore, shows that stainless steel, when used in the apparatus and in the method of this invention, functions to prevent poisoning of a platinum-tin promoted zinc aluminate catalyst utilized for butane and propane dehydrogenation as opposed to the use of quartz and other materials that were heretofore considered to be inert materials and, which, in fact, are not, when utilized in contact with this specific catalyst.

Other modifications and alterations of this invention will become apparent to those skilled in the art from the foregoing discussion, example and accompanying drawing, and it should be understood that this invention is not to be unduly limited thereto.

I claim:

1. A process for dehydrogenating a hydrocarbon feedstock comprising alkanes, cycloalkanes, arylalkanes or mixtures thereof in which the feedstock is dehydrogenated in contact with a layer of platinum-tin promoted zinc aluminate catalyst, said process comprising maintaining a first and a second layer of silica-free particles with the catalyst layer arranged between these layers of silica-free particles and passing the feed stream through one of said first and second layers of silica-free particles and thereafter through the catalyst layer.

2. A process in accordance with claim 1 wherein said feed stream is passed into a reactor having inlet and

TABLE

| Hold-Down Material: | Run I | Run II |
|---|---|---|
| 1/8" alundum pellets[a] | Yes | No |
| Stainless steel helices | No | Yes |
| Reactor Pressure, psig | 85 | 85 |
| Feed Stock was Isobutane: | | |
| Steam/iC$_4$ mol ratio | 16/1 | 16/1 |
| iC$_4$ Gas Hourly Space Velocity, V/V | 100 | 100 |
| Dehydrogenation Cycle, hrs. | 5 | 5 |
| Regeneration Cycle, hrs., (using air and steam) | 1/2 | 1/2 |
| Dehydrogenation Cycle Inlet Temp. ° F | 1010 to 1040 | 1040[b] to 1070 |
| After about 35 hours on dehydrogenation processing of isobutane to isobutene: | | |
| Conversion, mol %[c] | 44 | 55.4 |
| Selectivity, mol %[d] | 99.4 | 95.1 |

[a]Upon analysis the fresh alundum had a silica content (SiO$_2$) of 11.7 weight percent. Another portion of the alundum removed from the reactor after usage in the operation had a silica content (SiO$_2$) of only 11.3 weight percent.
[b]Slightly higher temperature used on invention Run II.
[c]By the term "Conversion" herein utilized it is meant mols of isobutane coverted/100 mols isobutane charged.
[d]By the term "Selectivity" herein utilized, it is meant mols of isobutene formed/100 mols of isobutane converted.

Comparison of Runs I and II, using alundum and stainless steel holddown solids, respectively, shows that the catalyst is sensitive to silica (silica being lost from alundum—silica migrates in steam at the conditions used).

outlet ends and wherein at least partially dehydrogenated feedstock is withdrawn from the outlet end of said reactor and wherein said first and second layers of silica-free particles separate said catalyst from the inlet and outlet ends of the reactor.

3. A process in accordance with claim 1 wherein said feed stream is passed through first and second layers of silica-free stainless steel particles.

* * * * *